Figure 1:
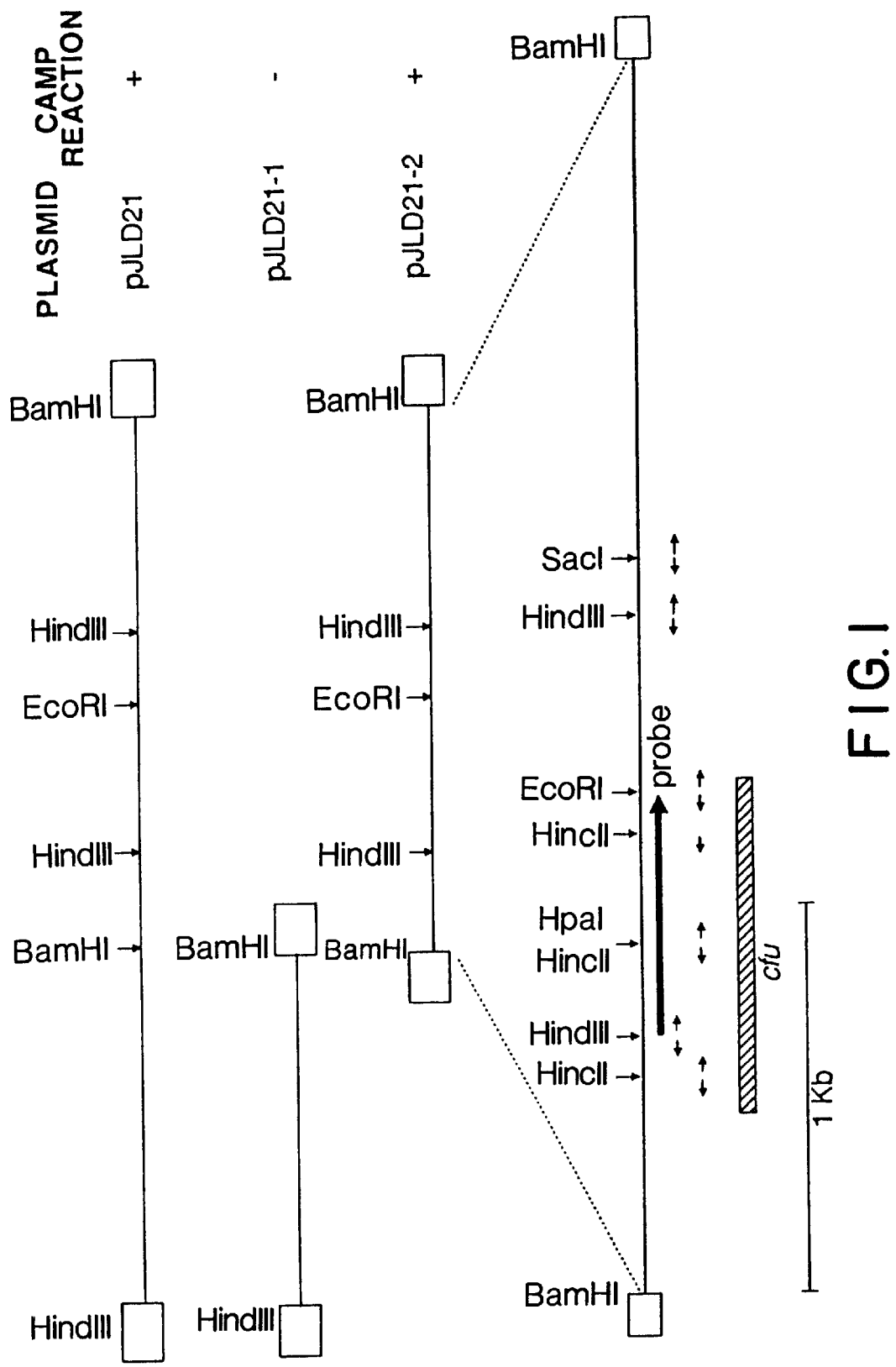

United States Patent [19]
Jiang et al.

[11] Patent Number: 5,863,543
[45] Date of Patent: Jan. 26, 1999

[54] CAMP FACTOR OF *STREPTOCOCCUS UBERIS*

[75] Inventors: Min Jiang; Andrew A. Potter; Philip Ronald MacLachlan, all of Saskatchewan, Canada

[73] Assignee: University of Saskatchewan, Saskatoon, Canada

[21] Appl. No.: 658,277

[22] Filed: Jun. 5, 1996

Related U.S. Application Data

[60] Provisional application No. 60/000,083 Jun. 8, 1995.
[51] Int. Cl.$^6$ .......................... A61K 39/09; A61K 38/00; C07K 14/315
[52] U.S. Cl. .................................... 424/244.1; 424/184.1; 424/185.1; 424/190.1; 424/130.1; 424/165.1; 514/2; 530/350; 530/820; 530/825; 530/412; 435/69.1; 435/69.3; 435/70.1; 435/71.1; 435/253.4
[58] Field of Search .............................. 424/244.1, 184.1, 424/185.1, 190.1, 130.1, 165.1; 530/350, 820, 825, 412; 514/2; 435/69.1, 69.3, 70.1, 71.1, 253.4

[56] References Cited

U.S. PATENT DOCUMENTS 4,879,213 11/1989 Fox et al. .

FOREIGN PATENT DOCUMENTS 0 626 452 A1 11/1994 European Pat. Off. .

OTHER PUBLICATIONS

Bernheimer et al., "Nature and mechanism of action of the CAMP protein of group B streptococci," *Inf. and Immunity* (*1979*) *23(3)*:838–844.
Christie et al., "A note on a lytic phenomenon shown by group B streptococci," *Aus. J. Exp. Bio. Med. Sci.* (*1944*) 22:197–200.
Fehrenbach et al., "Interaction of amphiphilic bacterial polypeptides with artificial membranes," *Bacterial Protein Tokins*, (1984):317–324.
Fehrenback et al., "Role of CAMP–factor (Protein B) for virulence," *Bacterial Protein Toxins, Zbl. Bakt. Suppl.* (*1988*) *17*:351–357.
Figura et al., "Differentiation of motile and mesophilic Aeromonas strains into species by testing for a CAMP–like factor," *J. Clin. Microbiol.* (*1987*) 25:1341–1342.
Fraser, "Bacteriology: Haemolytic activity of corynebacterium," *Nature* (*1961*) *189*:246.
Frey et al., "Cloning and Expression of a Cohemolysin, the CAMP Factor of *Actinobacillus pleuropneumoniae*," *Infection & Immunity* (*1989*) *57(7)*:2050–2056.
Jiang et al., Cloning, sequencing and expression of the CAMP factor gene of *Streptococcus uberis*, (1996) 20:297–307 incomplete.
Jurgens et al., "Purification and characterization of camp–factor form *Streptococcus Agalactiae* by hydrophobic interaction chromatography and chromatofocusing," *Jrn. of Chromatography*, (1985) 348:363–370.
Jurgens et al., "Unspecific binding of group B streptococcal cocytolysin (camp factor) to immunoglobulins and its possible role in pathogenicity," *J. Exp. Med.* (*1987*) *165*:720–732.
Kohler, W., "CAMP–like phenomena of vibrios," *Zentralbl. Bakteriol. Mikrobiol. Hyg. Ser. A* (*1988*) *270*:35–40.
Rocourt et al., "Notes; *Listeria welshimeri* sp. nov. and *Listeria seeligeri* sp. nov.," *Int. J. Syst. Bacteriol*, (1983) 33:866–869.
Ruhlmann et al., "Complete amino acid sequence of protein B," *Fed. of Europ. Biochem. Soc.* (*1988*) *235 (1,2)*:262–266.
Schneewind et al., "Cloning and Expression of the CAMP factor of group B streptococci in *Escherichia coli*," *Infection & Immunity* (*1988*) *56(8)*:2174–2179.
Skalka et al., "Lethal effect of CAMP–factor and UBERIS––factor–a new finding about diffusible exosubstances of *streptococcus agalactiae* and *streptococcus uberis*," *Zentralbl. Bakteriol. Ser. A* (*1981*) *249*:190–194.
Sterzik et al., "Interaction of the camp–factor from *S.agalactiae* with artificial membranes," *Bacterial Protein Toxins* (*1984*):195–196.
Sterzik et al., "Structure and function of CAMP factor of *streptococcus agalactiae*," *Zentralbl. Bakteriol. Mikrobiol. Hyg. Abt. 1* (*1985*) *15*:101–108.
Burgess et al J. Cell. Biol 1990 vol. III, 2129–2138.
Lazar et al Mol. Cell. Biol. 1988 vol. 8 (3), 1247–1252.

*Primary Examiner*—Paula K. Hutzell
*Assistant Examiner*—Khalzd Masood
*Attorney, Agent, or Firm*—Robins & Associates

[57] ABSTRACT

The CAMP factor gene of *Streptococcus uberis* (*S. uberis*) is described, as well as the recombinant production of CAMP factor therefrom. CAMP factors can be used in vaccine compositions for the prevention and treatment of bacterial infections.

6 Claims, 8 Drawing Sheets

```
                                                                                                     60
AATGAACATAAAATAAAAATTAATATTATATATTTTTATGATAATCACATATATTTGAC
                                                        -35

120
TTAAAAAAATTGTTACTGTATGATACAGGCATAAGTACTTATTTATTTTATAGATTGCAA
                    +1
                                      -10

180
TTTTATAAACAATTATATTTTTCAAAGAGGAATGCTT ATG GAA TTC AAA AAG TTA CTT TAT                                 8
                                      Met Glu Phe Lys Lys Leu Leu Tyr
                SD                        SIGNAL PEPTIDE_a_____a_>

TTA ACT GGT TCA ATC GCA GGA ATT ACT TTA TTT TCC CCA ATT ACT TTA ACA AGT GTC CAA GCA                  240
Leu Thr Gly Ser Ile Ala Gly Ile Thr Leu Phe Ser Pro Ile Leu Thr Ser Val Gln Ala>                      28
_a_____SIGNAL PEPTIDE_a_____a___|

AAT CAA ATA AAT GTT AGT CAA CCA TCT AAT AAT GAA AGT AAT GTT ATT TCA CAG AAA AAA                      300
Asn Gln Ile Asn Val Ser Gln Pro Ser Asn Asn Glu Ser Asn Val Ile Ser Gln Lys Lys>                      48
_b_____MATURE PEPTIDE_b_____b___|

GAA ATT GAT AAT AGT CTA AAT AGT GCT CAA GAA CTA TAT GCC TTG AAA GAA GAT                              360
Glu Ile Asp Asn Ser Leu Asn Ser Ala Gln Glu Leu Tyr Ala Leu Lys Glu Asp>                              68
_b_____MATURE PEPTIDE_b_____b___|

GTT AAA GGA ACT GAG AAA GAA CAA TCA GTT AAT TCA GCA ATT TCA GCT GTT GAA AAT TTA                      420
Val Lys Gly Thr Glu Lys Glu Gln Ser Val Asn Ser Ala Ile Ser Ala Val Glu Asn Leu>                      88
_b_____MATURE PEPTIDE_b_____b___|
```

FIG. 4A

```
AAA ACT TCA CTT AGA GCT AAT CCT GAA ACA ATT TAT GAT TTA AAT TCG ATT GGA ACA AGA      480
Lys Thr Ser Leu Arg Ala Asn Pro Glu Thr Ile Tyr Asp Leu Asn Ser Ile Gly Thr Arg>     108
 b   b   b   b   b   b   b   b   b   b   b   b   b   b   b   b   b   b   b   b
                                      MATURE PEPTIDE b   b   b   b   b   b   b

GTA GAA GCA ATC TCT GAC GTG ATT CAA GCA ATT GTT TTT TCA ACG CAA CAG TTA ACA AAT      540
Val Glu Ala Ile Ser Asp Val Ile Gln Ala Ile Val Phe Ser Thr Gln Gln Leu Thr Asn>     128
 b   b   b   b   b   b   b   b   b   b   b   b   b   b   b   b   b   b   b   b
MATURE PEPTIDE b   b   b   b   b   b   b   b   b   b   b   b   b   b   b   b

AAA GTT GAT CAA GCT CAC ATT GAT ATG GGA TTT GCT ATT ACG AAA TTA CTT ATT CGC ATT      600
Lys Val Asp Gln Ala His Ile Asp Met Gly Phe Ala Ile Thr Lys Leu Leu Ile Arg Ile>     148
 b   b   b   b   b   b   b   b   b   b   b   b   b   b   b   b   b   b   b   b
MATURE PEPTIDE b   b   b   b   b   b   b   b   b   b   b   b   b   b   b   b

GCA GAC CCA TTT GCT TCA AAT GAA TCC ATT AAA GGG CAA GTC GAA GCT GTT AAA CAA GTG      660
Ala Asp Pro Phe Ala Ser Asn Glu Ser Ile Lys Gly Gln Val Glu Ala Val Lys Gln Val>     168
 b   b   b   b   b   b   b   b   b   b   b   b   b   b   b   b   b   b   b   b
MATURE PEPTIDE b   b   b   b   b   b   b   b   b   b   b   b   b   b   b   b

CAA GCG ACT GTG CTT ACC TAT CCC GAT TTG CAG CCT ACG GAT AGA GCA ACT ATT TAC GTT      720
Gln Ala Thr Val Leu Thr Tyr Pro Asp Leu Gln Pro Thr Asp Arg Ala Thr Ile Tyr Val>     188
 b   b   b   b   b   b   b   b   b   b   b   b   b   b   b   b   b   b   b   b
MATURE PEPTIDE b   b   b   b   b   b   b   b   b   b   b   b   b   b   b   b

AAA TCA AAA TTA GAC AAG CTT ATT TGG CAA ACA AGA ATT ACC AGA GAT CAA AAA GTT CTT      780
Lys Ser Lys Leu Asp Lys Leu Ile Trp Gln Thr Arg Ile Thr Arg Asp Gln Lys Val Leu>     208
 b   b   b   b   b   b   b   b   b   b   b   b   b   b   b   b   b   b   b   b
MATURE PEPTIDE b   b   b   b   b   b   b   b   b   b   b   b   b   b   b   b

AAT GTA AAG AGT TTT GAA GTT TAT CAT CAA TTA AAT AAA GCT ATC ACA CAT GCA GTA GGT      840
Asn Val Lys Ser Phe Glu Val Tyr His Gln Leu Asn Lys Ala Ile Thr His Ala Val Gly>     228
 b   b   b   b   b   b   b   b   b   b   b   b   b   b   b   b   b   b   b   b
MATURE PEPTIDE b   b   b   b   b   b   b   b   b   b   b   b   b   b   b   b
```

FIG. 4B

```
GTA CAA TTA AAT CCA ACT GTA ACA GTT GCA CAA GTT GAC CAA GAA ATC AAA GTG CTA CAA    900
Val Gln Leu Asn Pro Thr Val Thr Val Ala Gln Val Asp Gln Glu Ile Lys Val Leu Gln>   248
 b       b       b       b       b       b       b       b       b       b
  MATURE PEPTIDE_b_____b_____b_____b_____b_____b_____b_____b_____>

GAA GCA TTA AAT ACT GCT CTA CAG TAAGGTAGAGATTGAATTGACGTATTAAAAAGGACT              960
Glu Ala Leu Asn Thr Ala Leu Gln>                                                  256
 b       b       b       b
 b_____MATURE PEPTIDE_b_____>

GGAATTTATTAATTTCAGTCCTTTAGAATTTTTATTTAGCTGATTTACTTGTTGAAGAGA                     1020

TTTGGTGGAAAATCAAGTACCATACTTCATTTCTCCCTCCAAATACTTGTATGTCGATTCC                    1080

CTTCTAAAACATAGCTAATTAGTTTAGTTTTCTGGCTAATAGATTGTACATGAAATTGTT                     1140

CAAAATTACTAGGGTAAAAGGTTTTCTTTTTATAAATTCATCATGACTAT                               1190
```

FIG.4C

```
SUCAMP   - MEFKKLLYLTGSIAGITLFSPILTSVQANQINVSQP------SNNESNVIS  -45
              :  :::  :   :  ::
SAGCAMP  -                                   DQVTTPQVVNHVNSNNQAQQMA  -22

SUCAMP   - QKKEEIDNSLNQESAQLYALKEDVKGTEKEQSVNSAISAVENLKTSLRAN  -95
             :: :  : ::: :  :  ::  :::::::
SAGCAMP  - QKL------DQDSIQLRNIKDNVQGTDYEKPVNEAITSVEKLKTSLRAN  -65

SUCAMP   - PETIYDLNSIGTRVEAISDVIQAIVFSTQQLTNKVDQAHIDMGFAITKLL  -145
             :: ::::::::::::: ::::::::::   :: :::::::::
SAGCAMP  - SETVYDLNSIGSRVEALTDVIEAITFSTQHLANKVSQANIDMGFGITKLV  -115

SUCAMP   - IRIADPFASNESIKGQVEAVKQVQATVLTYPDLQPTDRATIYVKSKLDKL  -195
           ::: :::::  ::: :  ::   : :::::::::::::::: ::::::
SAGCAMP  - IRILDPFASVDSIKAQVNDVKALEQKVLTYPDLKPTDRATIYTKSKLDKE  -165

SUCAMP   - IWQTRITRDQKVLNVKSFEVYHQLNKAITHAVGVQLNPTVTVAQVDQEIK  -245
           :: ::: ::::::::: :::  :::::::::::::::: ::  :::: :
SAGCAMP  - IWNTRFTRDKKVLNVKEFKVYNTLNKAITHAVGVQLNPNVTVQQVDQEIV  -215

SUCAMP   - VLQEALNTALQ  -256
            ::  :   ::
SAGCAMP  - TLQAALQTALK  -226
```

FIG. 6

CAMP FACTOR OF STREPTOCOCCUS UBERIS

CROSS-REFERENCE TO RELATED APPLICATION

This application is related to provisional patent application serial No. 60/000,083, filed Jun. 8, 1995, from which priority is claimed under 35 USC §119(e)(1) and which is incorporated herein by reference in its entirety.

TECHNICAL FIELD

The present invention relates generally to bacterial antigens. More particularly, the present invention pertains to the recombinant production of CAMP factor from *Streptococcus uberis* (*S. uberis*) and the use of CAMP factors in vaccine compositions.

BACKGROUND

*S. uberis* is an important cause of mastitis in dairy cattle and is responsible for about 20% of all clinical cases of mastitis (Bramley, A. J. and Dodd, F. H. (1984) *J. Dairy Res.* 51:481–512; Bramley, A. J. (1987) *Animal Health Nutrition* 42:12–16; Watts, J. L. (1988) *J. Dairy Sci.* 71:1616–1624). Since antimicrobial treatment is generally ineffective in treating *S. uberis* mastitis, the development of control measures must be based on an understanding of virulence factors and protective antigens involved in invasion and protection of the mammary gland (Collins et al. (1988) *J. Dairy Res.* 55:25–32; Leigh et al. (1990) *Res. Vet. Sci.* 49: 85–87; Marshall et al. (1986) *J. Dairy Res.* 53: 507–514).

It is known that some S. uberis strains can produce hyaluronic acid capsule (Hill, A. W. (1988) *Res. Vet. Sci.* 45:400–404), hyaluronidase (Schaufuss et al. (1989) *Zentralbl. Bakteriol. Ser.* A 271:46–53), R-like protein (Groschup, M. H. and Timoney, J. F. (1993) *Res. Vet. Sci.* 54:124–126), and a cohemolysin, the CAMP factor, also known as UBERIS factor (Skalka, B. and Smola, J. (1981) *Zentralbl. Bakteriol. Ser.* A 249:190–194). However, very little is known of their roles in pathogenicity.

The effect of CAMP factor was first described by Christie et al. in 1944 (Christie et al. (1944) *Aus. J. Exp. Biol. Med. Sci.* 22:197–200). These authors found that group B streptococci (GBS), such as *S. agalactiae*, produced a distinct zone of complete hemolysis when grown near the diffusion zone of the *Staphylococcus aureus* beta-toxin, sphingomyelinase. This phenomenon was called CAMP reaction and the compound for this reaction was characterized as the CAMP factor, an extracellular protein with a molecular weight of 23,500 (Bernheimer et al. (1979) *Infect. Immun.* 23:838–844). The CAMP factor was subsequently purified from *S. agalactiae* and characterized as a 25,000 Da protein with a pI of 8.9 (Jürgens et al. (1985) *J. Chrom.* 348:363–370). The amino acid sequence of *S. agalactiae* CAMP factor was determined by Rühlmann et al. (Rühlmann et al. (1988) *FEBS Lett* 235:262–266).

The mechanism of the CAMP reaction has been described. See, e.g., Bernheimer et al. (1979) *Infect. Immun.* 23:838–844; Sterzik et al. "Interaction of the CAMP factor from *S. agalactiae* with artificial membranes." In: Alouf et al., eds. *Bacterial protein toxins*, London: Academic Press Inc, 1984; 195–196; Sterzik et al. (1985) *Zentralbl. Bakteriol. Mikrobiol. Hyg. Abt.* 1 *Suppl.* 15:101–108; Fehrenbach et al. "Role of CAMP-factor (protein B) for virulence." In: Fehrenbach et al., eds. *Bacterial protein toxins*, Stuttgart: Gustav Fischer Verlag, 1988; 351–357; Fehrenbach et al. "Interaction of amphiphilic bacterial polypeptides with artificial membranes." In: Alouf et al., eds. *Bacterial protein toxins*, London: Academic Press Inc., 1984:317–324.

CAMP factor has lytic action on a variety of target cells including sheep and bovine erythrocytes, as well as on artificial membranes in which membrane phospholipids and sphingomyelin have been hydrolyzed by phospholipase or sphingomyelinase.

The role of CAMP factor in pathogenicity is unclear. A partially purified CAMP factor from *S. agalactiae* has been shown to be lethal to rabbits when injected intravenously (Skalka, B. and Smola, J. (1981) *Zentralbl. Bakteriol. Ser.* A 249:190–194). Furthermore, intraperitoneal injection of purified CAMP factor into mice has been shown to significantly raise the pathogenicity of a sublethal dose of group B streptococci (Fehrenbach et al. "Role of CAMP-factor (protein B) for virulence." In: Fehrenbach et al., eds. *Bacterial protein toxins*, Stuttgart: Gustav Fischer Verlag, 1988; 351–357). Additionally, like protein A of *S. aureus*, GBS CAMP factor can bind the Fc sites of immunoglobulins and has therefore been designated protein B (Jürgens et al. (1987) *J. Exp. Med.* 165:720–732).

In addition to GBS and S. uberis, other bacteria, including *Listeria monocytogenes* and *Listeria seeligeri* (Rocourt, J. and Grimont, P. A. D. (1983) *Int. J. Syst. Bacteriol.* 33:866–869) *Aeromonas sp.* (Figura, N. and Guglielmetti, P. (1987) *J. Clin. Microbiol.* 25:1341–1342), *Rhodococcus equi* (Fraser, G. (1961) *Nature* 189:246), and certain *Vibrio spp.* (Kohler, W. (1988) *Zentralbl. Bakteriol. Mikrobiol. Hyg. Ser.* A 270:35–40) produce reactions similar to the CAMP effect.

The CAMP factor genes of GBS and *A. pleuropneumoniae* have been cloned and expressed in *Escherichia coli* (Frey et al. (1989) *Infect. Immun.* 57:2050–2056; Schneewind et al. (1988) *Infect. Immun.* 56:2174–2179).

However, until now, the CAMP factor gene of *S. uberis* has not been cloned. Furthermore, the protective capability of CAMP factor has not been previously studied.

DISCLOSURE OF THE INVENTION

The present invention is based on the discovery of the CAMP factor gene of *S. uberis*, as well as the discovery that the CAMP factor is able to protect vertebrate subjects from infection. The CAMP factor, active immunogenic fragments thereof, active analogs thereof, or chimeric proteins including the same, can be used, either alone or in combination with other antigens, in novel subunit vaccines to provide protection from bacterial infection in vertebrate subjects.

Accordingly, in one embodiment, the subject invention is directed to an isolated nucleic acid molecule comprising a coding sequence for an immunogenic *Streptococcus uberis* CAMP factor. In additional embodiments, the invention is directed to recombinant vectors including the same, host cells transformed with these vectors and methods of recombinantly producing *S. uberis* CAMP factor.

In still further embodiments, the subject invention is directed to vaccine compositions comprising a pharmaceutically acceptable vehicle and an immunogenic CAMP factor. In particularly preferred embodiments, the CAMP factor is a Streptococcus CAMP factor.

In yet other embodiments, the present invention is directed to methods of treating or preventing bacterial infection, including streptococcal infections and mastitis, in a subject comprising administering to the subject a therapeutically effective amount of the above vaccine compositions.

In additional embodiments, the invention pertains to methods of producing vaccine compositions comprising (a) providing at least one immunogenic CAMP factor; and (b) combining the CAMP factor with a pharmaceutically acceptable vehicle.

These and other embodiments of the present invention will readily occur to those of ordinary skill in the art in view of the disclosure herein.

BRIEF DESCRIPTION OF THE FIGURES

FIG. 1 depicts restriction enzyme maps of recombinant plasmid pJLD21 and subclones thereof, designated pJLD21-1 and pJLD21-2. Lines indicate *S. uberis* insert DNA, while boxes represent the multiple cloning sites of vector pTZ18R. The CAMP activities of recombinant plasmid pJLD21 and its derived subclones are indicated on the right (+, CAMP reaction positive; –, CAMP reaction negative). The small horizontal arrows represent start points and directions of sequencing experiments. The probe fragment used for Southern blot experiments is indicated by the large arrow. The bar at the bottom indicates the location of the open reading frame of CAMP factor gene of *S. uberis* (cfu).

FIG. 2 shows the results of a CAMP reaction using *S. uberis* and recombinant *E. coli* clones. The CAMP reaction was done on a base #2 blood plate as described in the experimental section under Materials and Methods. Vertical streak: S, *Staphylococcus aureus*. Horizontal streak: 1, *S. uberis;* 2, *E. coli* JF1754(pTZ18R)(negative control); 3, *E. coli* JF1754(pJLD21)(CAMP-positive recombinant); 4, *E. coli* JF1754(pJLD21-2)(CAMP-positive subclone).

FIGS. 3A and 3B are representations of an SDS-PAGE and an immunoblot analysis, respectively, of *S. uberis* and *S. agalactiae* CAMP factors. FIG. 3A shows a coomassie blue-stained 12% polyacrylamide-SDS gel. Lane 1, partially purified *S. uberis* CAMP factor; lane 2, supernatant of *E. coli* JF1754(pJLD21) (CAMP positive); lane 3, supernatant of *E. coli* JF1754(pTZ18R) (CAMP negative); lane 4, supernatant of *S. agalactiae*; lane MW, prestained molecular weight standards. Numbers on the left of the figure indicate the positions of the molecular weight markers (in thousands). FIG. 3B shows an immunoblot of the gel presented in FIG. 3A. Samples were transferred to a nitrocellulose membrane and reacted with mouse antiserum against purified *S. uberis* CAMP factor.

FIGS. 4A–4C (SEQ ID NOS: 1–2) show the nucleotide sequence of *S. uberis* CAMP factor gene and its promoter region. The start site of transcription is represented by +1, and the –10 and –35 regions of the promoter are indicated by the underlines. The putative Shine-Dalgarno sequence is shown as SD. The deduced amino acid sequence of *S. uberis* CAMP factor is shown using the three-letter code below the nucleotide sequence. The signal peptide and mature peptide are specified.

FIG. 5 shows a primer extension analysis of the promoter region of the *S. uberis* CAMP factor gene. The primer extension reactions were done as described in the examples. The cellular RNAs used were obtained from *S. uberis* (lane 1), *E. coli* JF1754(pJLD21) (lane 2), and *E. coli* JF1754 (pTZ18R) (lane 3). A dideoxy sequencing ladder was generated by using the same primer and is shown as T, G, C, A above each lane.

FIG. 6 (SEQ ID NOS:3–4) shows a comparison between *S. uberis* CAMP factor (upper lines, designated as "SUCAMP") and *S. agalactiae* CAMP factor (low lines, designated as "SAGCAMP"). Amino acids are identified in the single-letter code. Identical amino acids are indicated by double dots (:). The aligned sequences show 66.4% identity. Spaces (indicated by dash) were introduced in the sequences to optimize alignment.

FIG. 7 shows a Southern blot analysis of different *S. uberis* strains. The origin of the probe used is indicated in FIG. 1; chromosomal DNA from each *S. uberis* strain was cut with HindIII. Lanes 1, 2, 3 and 4 are the DNA samples from ATCC strains 9927, 13386, 13387 and 19436, respectively; lanes 5, 6, 7 and 8 are the DNA samples from field isolates. The arrowhead on the right indicates the position and size of the hybridizing restriction enzyme fragments. CAMP reaction phenotype of each strain is indicated at the bottom by "+" (CAMP reaction positive) and "–" (CAMP reaction negative).

FIG. 8 depicts the construction of pGH-CAMP. The CAMP reactions for each clone from which the plasmid was derived are shown to the right of the figure; + indicates a positive reaction and – a negative reaction. Open boxes indicate pTZ18R and hatched boxes indicate pGH433.

DETAILED DESCRIPTION

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

A. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a CAMP factor" includes a mixture of two or more CAMP factors, and the like.

The term "CAMP factor" or a nucleotide sequence encoding the same, intends a protein or a nucleotide sequence, respectively, which is derived from a CAMP factor gene found in a variety of bacterial species, including, without limitation Streptococcus uberis, group B streptococci (GBS) such as *S. agalactiae* (Jürgens et al. (1985) *J. Chromatogr.* 348:363–370; and Rühlmann et al. (1988) *FEBS Lett* 235:262–266), *Listeria monocytogenes* and *Listeria seeligeri* (Rocourt, J. and Grimont, P. A. D. (1983) *Int. J. Syst. Bacteriol.* 33:866–869), *Aeromonas sp.* (Figura, N. and Guglielmetti, P. (1987) *J. Clin. Microbiol.* 25:1341–1342), Rhodococcus equi (Fraser, G. (1961) *Nature* 189:246), and certain *Vibrio spp.* (Kohler, W. (1988) *Zentralbl. Bakteriol. Mikrobiol. Hyg. Ser*. A 270:35–40).

A representative CAMP factor gene, derived from *S. uberis*, is found in plasmid pJLD21 (ATCC Accession No. 69837) and depicted in FIGS. 4A–4C (SEQ ID NOS: 1–2).

The derived protein or nucleotide sequences need not be physically derived from the gene described above, but may be generated in any manner, including for example, chemical synthesis, isolation (e.g., from an organism that produces the CAMP factor) or by recombinant production, based on the information provided herein.

Furthermore, the term intends proteins having amino acid sequences substantially homologous to contiguous amino acid sequences encoded by the genes, which display immunological activity. Thus, the terms include full-length, as well as immunogenic and truncated and partial sequences, as well as active analogs and precursor forms of the proteins, such as those forms including the signal sequence, described more fully below.

The terms also include proteins in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids (both those occurring naturally with the molecule or other lipids that do not destroy immunological activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The term therefore intends deletions, additions and substitutions to the sequence, so long as the polypeptide functions to produce an immunological response as defined above. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity of the protein, are therefore within the definition of the reference polypeptide.

The term "streptococcal CAMP factor" intends a CAMP factor, as defined above, derived from a streptococcal species that produces the same, including *S. uberis* and GBS such as *S. agalactiae*. An "*S. uberis* CAMP factor" is a CAMP factor as defined above, derived from *S. uberis*.

By "mastitis" is meant an inflammation of the mammary gland in mammals, including in cows, ewes, goats, sows, mares, and the like, caused by various bacteria that produce CAMP factors, described more fully below. The infection manifests itself by the infiltration of phagocytic cells in the gland. Generally, 4 clinical types of mastitis are recognized: (1) peracute, associated with swelling, heat, pain, and abnormal secretion in the gland and accompanied by fever and other signs of systemic disturbance, such as marked depression, rapid weak pulse, sunken eyes, weakness and complete anorexia; (2) acute, with changes in the gland similar to those above but where fever, anorexia and depression are slight to moderate; (3) subacute, where no systemic changes are displayed and the changes in the gland and its secretion are less marked: and (4) subclinical, where the inflammatory reaction is detectable only by standard tests for mastitis.

Standard tests for the detection of mastitis include but are not limited to, the California Mastitis Test, the Wisconsin Mastitis Test, the Nagase test, the electronic cell count and somatic cell counts used to detect a persistently high white blood cell content in milk. In general, a somatic cell count of about 300,000 to about 500,000 cells per ml or higher, in milk will indicate the presence of infection. Thus, a vaccine is considered effective in the treatment and/or prevention of mastitis when, for example, the somatic cell count in milk is retained below about 500,000 cells per ml. For a discussion of mastitis and the diagnosis thereof, see, e.g., *The Merck Veterinary Manual. A Handbook of Diagnosis, Therapy, and Disease Prevention and Control for the Veterinarian*, Merck and Co., Rahway, N.J., 1991.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "epitope" refers to the site on an antigen or hapten to which specific B cells and T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or $\gamma\delta$ T cells, directed specifically to an antigen or antigens included in the composition or vaccine of interest. Preferably, the host will display a protective immunological response to the CAMP factor in question, e.g., the host will be protected from subsequent infection by the pathogen and such protection will be demonstrated by either a reduction or lack of symptoms normally displayed by an infected host or a quicker recovery time.

The terms "immunogenic" protein or polypeptide refer to an amino acid sequence which elicits an immunological response as described above. An "immunogenic" protein or polypeptide, as used herein, includes the full-length sequence of the CAMP factor in question, including the precursor and mature forms, analogs thereof, or immunogenic fragments thereof. By "immunogenic fragment" is meant a fragment of a CAMP factor which includes one or more epitopes and thus elicits the immunological response described above. Such fragments can be identified by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol. 23:709–715*, all incorporated herein by reference in their entireties.

Immunogenic fragments, for purposes of the present invention, will usually be at least about 2 amino acids in length, more preferably about 5 amino acids in length, and most preferably at least about 10 to 15 amino acids in length. There is no critical upper limit to the length of the fragment, which could comprise nearly the full-length of the protein sequence, or even a fusion protein comprising two or more epitopes of the CAMP factor or factors in question.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "vector" is a replicon, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated. "Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

Similarly, a coding sequence is "operably linked to" another coding sequence (i.e., in the case of a chimeric protein) when RNA polymerase will transcribe the two coding sequences into mRNA, which is then translated into the polypeptides encoded by the two coding sequences. The coding sequences need not be contiguous to one another so long as the transcribed sequence is ultimately processed to produce the desired protein.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs such as ALIGN, Dayhoff, M. O. (1978) in *Atlas of Protein Sequence and Sturcture* 5:Suppl. 3, National biomedical Research Foundation, Washington, D.C.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

The term "functionally equivalent" intends that the amino acid sequence of the CAMP factor is one that will elicit a substantially equivalent or enhanced immunological response, as defined above, as compared to the response elicited by a CAMP factor having identity with either the mature sequence for the reference CAMP factor, or an immunogenic portion thereof.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

The term "treatment" as used herein refers to either (i) the prevention of infection or reinfection (prophylaxis), or (ii) the reduction or elimination of symptoms of the disease of interest (therapy).

By "vertebrate subject" is meant any member of the subphylum chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age. Thus, both adult and newborn animals, as well as fetuses, are intended to be covered.

B. General Methods

Central to the present invention is the discovery that the CAMP factor is capable of eliciting a protective immune response in a vertebrate subject. The gene for the S. uberis CAMP factor has been isolated and characterized and the CAMP factor encoded thereby sequenced. The protein product from the S. uberis CAMP factor gene has been shown to protect cattle from subsequent challenge with S. uberis.

In particular, the complete DNA sequence of S. uberis CAMP factor is shown in FIGS. 4A–4C (SEQ ID NO: 1–2). A major transcript of the CAMP factor gene is found beginning with an "A" residue (depicted at the +1 position in FIG. 4A). ±10 and ±35 regions, characteristic of E. coli promoters (Harley, C. B. and Reynolds, R. P. (1987) Nucleic Acids Res. 15:2343–2361), are found upstream of the transcriptional start site, as indicated in FIG. 4A. An open reading frame beginning with an ATG codon is located at positions 157 to 159 and terminates with a TAA stop codon at positions 925 to 927. The ATG start codon is preceded by the purine-rich sequence AAGAGG, which serves as a ribosome binding site in E. coli (Stormo et al. (1982) Nucleic Acids Res. 10:2971–2996).

As shown in FIGS. 4A–4C, the S. uberis CAMP factor gene encodes a preprotein of about 256 amino acids (amino acid residues 1 through 256, inclusive, of FIGS. 4A–4C) that includes an N-terminal signal sequence approximately 28 amino acids in length. The precursor molecule has a calculated molecular weight of 28,363 Da. The mature S. uberis CAMP factor thus includes amino acid residues 29 through 256, inclusive, as depicted in FIGS. 4A–4C. As discussed further below, the portion of the CAMP factor gene encoding the signal sequence can be included in constructs that encode the CAMP factor to direct secretion of the CAMP factor upon expression. Additionally, the CAMP factor signal sequence and the nucleic acid sequence encoding the same can be used with heterologous proteins and nucleic acid molecules, to aid in the secretion thereof.

As shown in FIG. 6 (SEQ ID NOS: 3–4), alignment of the 226-amino acid sequence of the S. agalactiae CAMP factor with the deduced 256 amino acids of the S. uberis CAMP factor shows that 66.4% of the amino acid residues are identical. Additionally, antibodies raised against purified S. uberis CAMP factor cross-react with S. agalactiae protein B. As shown in the examples, the S. uberis CAMP factor is secreted when produced recombinantly in E. coli.

The exact localization and sequence of the CAMP factor gene allows for in vitro mutagenesis studies to assess the functions of different domains on the CAMP protein. Also, the present data permits the generation of stable CAMP factor-synthesis deficient mutants through gene replacement and other molecular techniques. Comparison of the virulence of native and mutant S. uberis strains in animals provides important information regarding the contribution of the CAMP factor to the pathogenicity of bacteria expressing CAMP factors.

The CAMP factors, immunogenic fragments thereof or chimeric proteins including the same, can be provided in subunit vaccine compositions. In addition to use in vaccine compositions, the proteins or antibodies thereto can be used as diagnostic reagents to detect the presence of infection in a vertebrate subject. Similarly, the genes encoding the proteins can be cloned and used to design probes to detect and isolate homologous genes in other bacterial strains.

The vaccine compositions of the present invention can be used to treat or prevent a wide variety of bacterial infections in vertebrate subjects. For example, vaccine compositions including CAMP factors from S. uberis and/or group B streptococci (GBS), such as S. agalactiae, can be used to treat streptococcal infections in vertebrate subjects that are caused by these species. In particular, S. uberis and S. agalactiae are common bacterial pathogens associated with mastitis in bovine, equine, ovine and goat species. Additionally, group B streptococci, such as S. agalactiae, are known to cause numerous other infections in vertebrates, including septicemia, meningitis, bacteremia, impetigo, arthritis, urinary tract infections, abscesses, spontaneous abortion etc. Hence, vaccine compositions containing streptococcal CAMP factors will find use in treating and/or preventing a wide variety of streptococcal infections.

Similarly, CAMP factors derived from Listeria monocytogenes and L. seeligeri, Aeromonas sp., Rhodococcus equi, and Vibrio spp. will find use for treating bacterial infections caused by these species. For example, CAMP factors can be used to prevent or treat listeriosis in a wide range of animals and birds, including humans. The infection can manifest itself as encephalitis and meningoencephalitis in ruminants and avian species such as geese, chickens, turkeys, ducks, canaries and parrots; septicemia in monogastric animals, neonatal ruminants and poultry; and spontaneous abortion and latent infections in a wide variety of animals. Aeromonas causes infections in fish, including in salmonids, aquarium fish, goldfish, freshwater and marine fish; as well as infections in caged birds and in amphibians and reptiles. Rhodococcus equi causes respiratory infections, lymphangitis, peritonitis, enteritis, abscesses and spontaneous abortion in horses. Vibrio causes vibriosis in many cultured, aquarium and wild marine and estuarine fish; infections of open wounds in cetaceans; and avian vibrionic hepatitis and avian infectious hepatitis in chickens.

Thus, it is readily apparent that CAMP factor vaccines can be used to treat and/or prevent a wide variety of bacterial infections in numerous species.

CAMP factors from various species can be used either alone or in combination in the vaccine compositions of the present invention. For example, it will sometimes be preferable to have more than one epitope of one or more of the CAMP factors in the vaccine compositions of the present invention so that the subject in question can be provided with a broad spectrum of protection against infection. In its simplest form, this can be achieved by employing a polypeptide encoding the complete sequence of one of the CAMP factors, or by employing a combination of polypeptides encoding the sequences of two or more of the CAMP factors or epitopes of the CAMP factors. Thus, the vaccine compositions could comprise, for example various combinations of one or more of the CAMP factors, or a combination of several of the CAMP factors, or even several epitopes derived from the CAMP factors.

Furthermore, the vaccine compositions of the present invention can include other bacterial, fungal, viral or protozoal antigens. These antigens can be provided separately of even as fusion proteins comprising fragments of one or more of the CAMP factors fused to these antigens.

Production of the CAMP Factors

The above described CAMP factors and active fragments, analogs and chimeric proteins derived from the same, can be produced by a variety of methods. Specifically, the CAMP factors can be isolated directly from bacteria which express the same. This is generally accomplished by first preparing a crude extract which lacks cellular components and several extraneous proteins. The desired proteins can then be further purified i.e. by column chromatography, HPLC, immunoadsorbent techniques or other conventional methods well known in the art.

More particularly, techniques for isolating CAMP factors have been described in e.g., Skalka, B. and Smola, J. (1981) *Zbl. Bakt. Hyg., I. Abt. Orig.* A249:190–194; Skalka et al. (1980) *Zbl. Vet. Med.* B27:559–566; Skalka et al. (1979) *Zbl. Vet. Med.* B26:679–687; Bernheimer et al. (1979) *Infect. Immun.* 23:838–844; Jürgens et al. (1985) *J. Chrom.* 348:363–370; Jürgens et al. (1987) *J. Exp. Med.* 165:720–732.

Alternatively, the proteins can be recombinantly produced as described herein. As explained above, these recombinant products can take the form of partial protein sequences, full-length sequences, precursor forms that include signal sequences, mature forms without signals, or even fusion proteins (e.g., with an appropriate leader for the recombinant host, or with another subunit antigen sequence for Streptococcus or another pathogen).

The CAMP factor genes of the present invention can be isolated based on the ability of the protein products to display CAMP activity, using CAMP assays as described below. Thus, gene libraries can be constructed and the resulting clones used to transform an appropriate host cell. Colonies can be pooled and screened for clones having CAMP activity. Colonies can also be screened using polyclonal serum or monoclonal antibodies to the desired antigen.

Alternatively, once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; Sambrook et al., supra. Once a clone from the screened library has been identified by positive hybridization, it can be confirmed by restriction enzyme analysis and DNA sequencing that the particular library insert contains the desired CAMP factor gene or a homolog thereof.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; Sambrook et al., supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If signal sequences are included, they can either be the native, homologous sequences, or heterologous sequences. For example, the signal sequence for *S. uberis* CAMP factor (shown in FIG. 4A), can be used for secretion of various CAMP factors, as can a number of other signal sequences, well known in the art. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the CAMP factor of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus spp.*, will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes* aegypti, Autographa californica, Bombyx mori, Drosophila melanogaster, Spodoptera frugiperda, and Trichoplusia ni.

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The CAMP factors, fragments, analogs and chimeras containing the same, can be tested for CAMP activity using any of several standard tests. For example, CAMP factors are known to display lytic action on a variety of target cells including bovine and ovine erythrocytes. Thus, a convenient method for testing for CAMP factor activity utilizes standard hemolytic reactions using ovine or bovine erythrocytes. See, e.g., Christie et al. (1944) *Aus. J. Exp. Biol. Med. Sci.* 22:197–200; Brown et al. (1974) *Infect. Immun.* 9:377–383; Darling, C. L. (1975) *J. Clin. Microbiol.* 1:171; Wilkinsin, H. W. (1977) *J. Clin. Microbiol.* 6:42; Bernheimer et al. (1979) *Infect. Immun.* 23:838–844; Skalka, B. and Smola, J. (1981) *Zbl. Bakt. Hyg., I. Abt. Orig.* A249:190–194; Huser et al. (1983) *J. Gen. Microbiol.* 129:1295.

Activity can also be tested by monitoring the release of entrapped marker molecules from liposomes made from materials susceptible to disruption by CAMP factors. For example, CAMP activity can be monitored using [$^{14}$C] glucose-containing liposomes prepared from, e.g., sphingomyelin, cholesterol and dicetyl phosphate, and measuring the release of trapped [$^{14}$C]glucose due to disruption of the liposomes by the CAMP factor. See, e.g., Bernheimer et al. (1979) *Infect. Immun.* 23:838–844. Similarly, ATP release from liposomes in the presence of CAMP factor can be monitored as described in Sterzik et al. (1984) "Interaction of the CAMP factor from *S. agalactiae* with artificial membranes" In: Alouf et al., eds. *Bacterial protein toxins*, London: Academic Press Inc., 1984:195–196; and Sterzik et al. (1985) *Zentralbl. Bakteriol. Mikrobiol. Hyg. Abt. 1 Suppl.* 15:101–108. See, also Fehrenbach et al. (1984) "Interaction of amphiphilic bacterial polypeptides with artificial membranes." In: Alouf et al., eds. *Bacterial protein toxins*, London: Academic Press Inc., 1984:317–324.

The CAMP factors of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J. Chrom.* 348:363–370. If serum containing polyclonal antibodies is used, the polyclonal antibodies can be purified by immunoaffinity chromatography, using known procedures.

Monoclonal antibodies to the CAMP factors and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the CAMP factor of interest, or fragment thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response.

Vaccine Formulations and Administration

The CAMP factors of the present invention can be formulated into vaccine compositions, either alone or in combination with other antigens, for use in immunizing subjects as described below. Methods of preparing such formulations are described in, e.g., *Remington's Pharmaceutical Sciences*, Mack Publishing Company, Easton, Pa., 18 Edition, 1990. Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, avridine, aluminum hydroxide, dimethyldioctadecyl ammonium bromide (DDA), oils, oil-in-water emulsions, saponins, cytokines, and other substances known in the art.

The CAMP factor may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The CAMP factors may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the CAMP factors of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the CAMP factors (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectable vaccine formulations will contain a "therapeutically effective amount" of the active ingredient, that is, an amount capable of eliciting an immune response in a subject to which the composition is administered. In the treatment and prevention of mastitis, for example, a "therapeutically effective amount" would preferably be an amount which controls infection, as measured by, e.g. the ability of the composition to retain or bring the somatic cell count in milk below about 500,000 cells per ml. The exact amount is readily determined by one skilled in the art using standard tests. The CAMP factor will typically range from about 1% to about 95% (w/w) of the composition, or even higher or lower if appropriate. With the present vaccine formulations, 20 to 500 $\mu$g of active ingredient per ml of injected solution should be adequate to raise an immunological response when a dose of 1 to 3 ml per animal is administered.

To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to infection.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The CAMP factors can also be delivered using implanted mini-pumps, well known in the art.

The CAMP factors of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK⁻ recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject CAMP factors can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al. (1990) *Science* 247:1465–1468). Liposome-mediated gene transfer can also be accomplished using known methods. See, e.g., Hazinski et al. (1991) *Am. J. Respir. Cell Mol. Biol.* 4:206–209; Brigham et al. (1989) *Am. J. Med. Sci.* 298:278–281; Canonico et al. (1991) Clin. Res. 39:219A; and Nabel et al. (1990) *Science* 1990) 249:1285–1288. Targeting agents, such as antibodies directed against surface antigens expressed on specific cell types, can be covalently conjugated to the liposomal surface so that the nucleic acid can be delivered to specific tissues and cells susceptible to infection.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md., under the provisions of the Budapest Treaty. The accession number indicated was assigned after successful viability testing, and the requisite fees were paid. The designated deposits will be maintained for a period of thirty (30) years from the date of deposit, or for five (5) years after the last request for the deposit, whichever is longer. Should a culture become nonviable or be inadvertently destroyed, or, in the case of plasmid-containing strains, lose its plasmid, it will be replaced with a viable culture(s) of the same taxonomic description.

Should there be a discrepancy between the sequence presented in the present application and the sequence of the gene of interest in the deposited plasmid due to routine sequencing errors, the sequence in the deposited plasmid controls.

| Strain | Deposit Date | ATCC No. |
| --- | --- | --- |
| pJLD21 in E. coli JF1754 | June 9, 1995 | 69837 |

C. Experimental

Materials and Methods

Enzymes were purchased from commercial sources, and used according to the manufacturers' directions. Radionucleotides and nitrocellulose filters were also purchased from commercial sources.

In the isolation of DNA fragments, except where noted, all DNA manipulations were done according to standard procedures. See, Sambrook et al., supra. Restriction enzymes, T$_4$ DNA ligase, E. coli, DNA polymerase I, Klenow fragment, and other biological reagents can be purchased from commercial suppliers and used according to the manufacturers' directions. Double stranded DNA fragments were separated on agarose gels.

Bacterial strains, plasmids and growth conditions:

The E. coli strain used for cloning the S. uberis CAMP factor gene was JF1754 (hsdR lac gal metB leuB hisB) (McNeil, J. B. and Friesen, J. D. (1981) Mol. Gen. Genet. 184:386–393). Competent E. coli JF1754 was made as previously described (Hanahan, D. "Techniques for transformation of E. coli." In: Glover D M, ed. DNA cloning (Volume I): a practical approach. Oxford: IRL Press, 1985:109–135). E. coli cells were grown in Luria broth (Difco Laboratories) or on Luria-agar (Difco Laboratories) plates. Ampicillin was used at 50 μg/ml for the growth of E. coli strains containing recombinant plasmids. Four S. uberis strains, as well as S. agalactiae and S. aureus, were obtained from the American Type Culture Collection (ATCC Accession Nos. 9927, 13386, 13387, 19436, 27541 and 25923, respectively). Other S. uberis strains are field isolates kindly provided by M. Chirino-Trejo, University of Saskatchewan. All streptococcal strains were grown in brain heart infusion broth (BHI, Difco Laboratories) or on base #2 blood agar plates with 5% sheep blood (PML microbiologicals).

The cloning vector pTZ18R (Mead et al. (1986) Protein Eng. 1:67–74) was obtained from Pharmacia Canada Ltd.

Preparation of S. aureus beta-toxin:

S. aureus was cultured in BHI for 18 h at 37° C. and the supernatant obtained after centrifugation at 5,000 g was sterilized by filtration through a 0.22-uM filter (Nalge company). This material, referred to as crude beta-toxin, was stored at −20° C.

CAMP reaction

Bacteria were screened for CAMP activity as described (Schneewind et al. (1988) Infect. Immun. 56:2174–2179). Briefly, strains were streaked perpendicular to a streak of beta-toxin-producing S. aureus on blood agar plates and after 6 h–20 h incubation at 37° C., they were observed for hemolysis.

Purification of CAMP factor

CAMP factor was partially purified from the culture supernatant of S. uberis (ATCC Accession No. 9927) by Octyl-Sepharose CL-4B (Pharmacia) chromatography as described by Jürgens et al. (1985) J. Chrom. 348:363–370.

Polyclonal antibodies

To analyse the recombinant CAMP factor of S. uberis, polyclonal antibodies directed against the purified CAMP factor were obtained. Mice were immunized by intraperitoneal injection of 20 μg of the purified CAMP protein with complete Freund adjuvant. This primary immunization was followed 3 weeks later by the second intraperitoneal injection of the same amount of CAMP protein with incomplete Freund adjuvant and another 3 weeks later by the third intravenous injection of 20 μg of CAMP protein with incomplete Freund adjuvant. The blood serum samples were then taken 10 days later.

PAGE and immunoblotting Protein samples of S. agalactiae and E. coli were obtained from culture supernatants by trichloroacetic acid (TCA)-precipitation at a final concentration of 10%. SDS-polyacrylamide gel electrophoresis (PAGE) of proteins was performed as described by Laemmli (Laemmli, U. K. (1970) Nature 227:680–685). Proteins were electroblotted onto nitrocellulose membranes as recommended by the supplier (Bio-Rad) and the blots were developed as described elsewhere (Theisen, M. and Potter, A. A. (1992) J. Bacteriol. 174:17–23) with the following differences. The first antiserum used was mouse polyclonal antiserum against partially-purified S. uberis CAMP protein, and it was absorbed with antigens of the E. coli host strain as described previously (Frey et al. (1989) Infect. Immun. 57:2050–2056). The second antibody used in blotting procedure was the goat anti-mouse IgG coupled to alkaline phosphatase (Kirkegaard & Perry Laboratories, Inc.).

DNA manipulations

All molecular techniques were as recommended by the supplier (Pharmacia Canada Ltd.) or Sambrook et al., supra. Chromosomal DNA of S. uberis was prepared from cells grown in 100 ml BHI plus 5% (w/v) glycine. Cells were pelleted and resuspended in 2.5 ml of TES buffer (30 mM Tris-HCl, 5 mM EDTA, 50 mM NaCl; pH 8.0) with 25% sucrose and 1.6 mg/ml lysozyme (Sigma). The suspension was incubated for 1 h at 37° C., followed by freezing at −70° C. The frozen cells were thawed in a 65° C. water bath. EDTA and proteinase K (Pharmacia) were added to final concentrations of 20 mM and 1.2 mg/ml, respectively, before incubation at 65° C. for 30 min. To lyse cells completely, sarkosyl was added to 1% and incubated at 37° C. for 1 h. Two ml of TE buffer (10 mM Tris-HCl, 1 mM EDTA; pH 8.9) was added prior to phenol: chloroform extraction. DNA was recovered by ethanol precipitation and was treated with RNase (Pharmacia Canada Ltd.).

Size-fractionated Sau3AI-digested chromosomal DNA fragments were isolated by sucrose density gradient centrifugation (Sambrook et al., supra).

DNA sequence was determined by the dideoxy-chain termination method of Sanger et al. (1977) Proc. Natl. Acad. Sci. USA 74:5463–5467 on double-stranded plasmid templates by using a T7 Sequencing kit (Pharmacia Canada Ltd.).

RNA analyses

RNA from E. coli strains was isolated as described previously (Lloubes et al. (1986) Nucleic Acid Res. 14:2621–2636) with an additional RNase-free DNase I digestion. RNA from S. uberis was prepared as follows. The cell pellet from a 10 ml culture ($OD_{600}$=0.6) was resuspended in 250 μl of TE buffer (pH 8.0) containing 500 u of mutanolysin (Sigma) and incubated at 37° C. for 30 min. Lysis buffer (250 μl)(60 mM Tris-HCl pH 7.4, 200 mM NaCl, 10 mM EDTA, 2% SDS) and 100 μg/ml (final concentration) of proteinase K was added and the incubation continued for 1 h. The sample was extracted once with 65° C. phenol (water saturated, pH 4.0) and twice with room temperature phenol. RNA was recovered by ethanol precipitation and treated with DNase I (Pharmacia Canada Ltd.).

Primer extension assay was performed as described by Miller et al. (1986) Nucleic Acids Res. 14:7341–60. RNasin and moloney murine leukemia virus reverse transcriptase were obtained from Pharmacia Canada Ltd.

EXAMPLE 1

Cloning and Expression of the S. uberis CAMP Factor Gene

Chromosomal DNA of S. uberis (ATCC 9927) was partially digested with Sau3AI and size fractionated in a sucrose gradient; from this, 2- to 5-kb DNA fragments were recovered. The ends of these fragments were partially filled in with dGTP and dATP and ligated into pTZ18R which was cut with SalI and partially filled in with dTTP and dCTP. Following transformation of E. coli JF1754 competent cells, clones expressing the CAMP factor gene were identified on blood plates with ampicillin and beta-toxin on the surface. Six clones from a total of 10,000 were phenotypically hemolytic and each one mediated a distinct CAMP reaction. One of them, containing recombinant plasmid pJLD21, was selected for further study and its CAMP reaction is shown in FIGS. 1 and 2.

Figure 2:
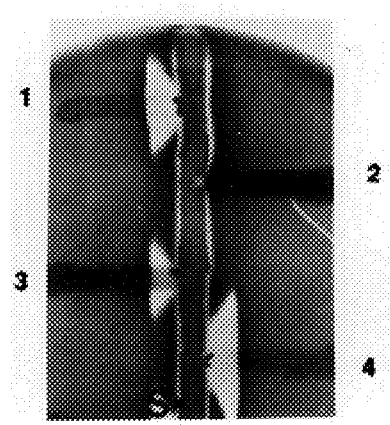

Plasmid pJLD21 contained a 5.2 kb insert fragment and the CAMP factor gene, cfu, was localized within a 3.2 kb BamHI fragment after the CAMP-positive subclone pJLD21-2 was generated (FIGS. 1 and 2). This subclone was further analysed with more restriction enzymes for sequencing purposes.

Figures 3A, 3B:
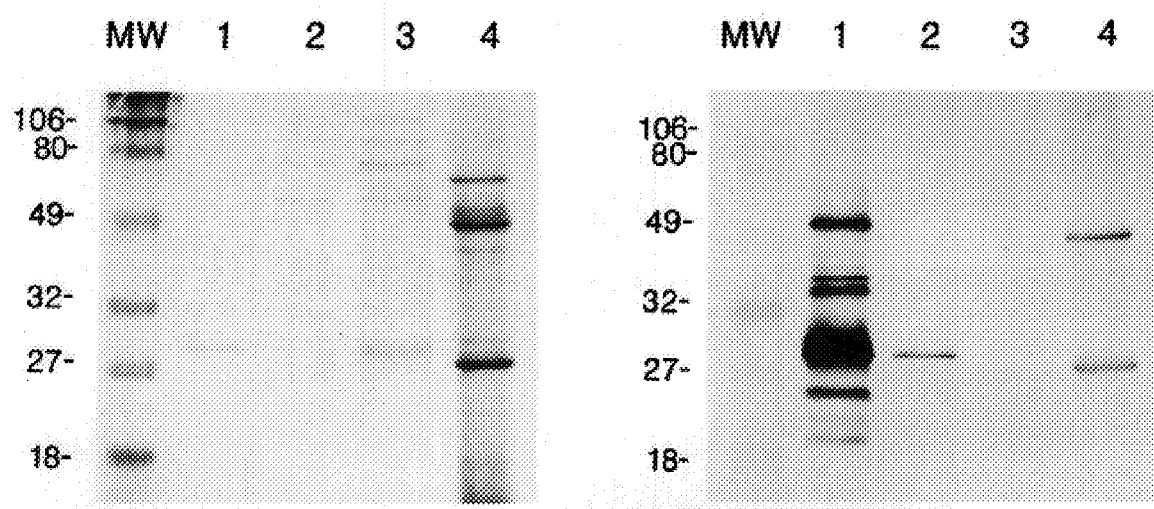

To study the expression of the recombinant CAMP factor, SDS-PAGE analysis of supernatant proteins from Cfu$^+$ E. coli JF1754 (pJLD21) and host E. coli JF1754 (pTZ18R) was performed (FIG. 3A). Compared to the vector control, no distinguishable band was observed in the lane containing supernatant from the Cfu$^+$ clone, indicating that either expression was at a very low level or the protein was not secreted efficiently. To identify the CAMP factor encoded by pJLD21, the proteins separated by SDS-PAGE were transferred to a nitrocellulose membrane and immunoblotted (FIG. 4B). The Cfu$^+$ E. coli clone carrying pJLD21 expressed a protein with molecular weight of 28,000 (lane 2), similar to the native CAMP factor of S. uberis (lane 1).

Figure 8:
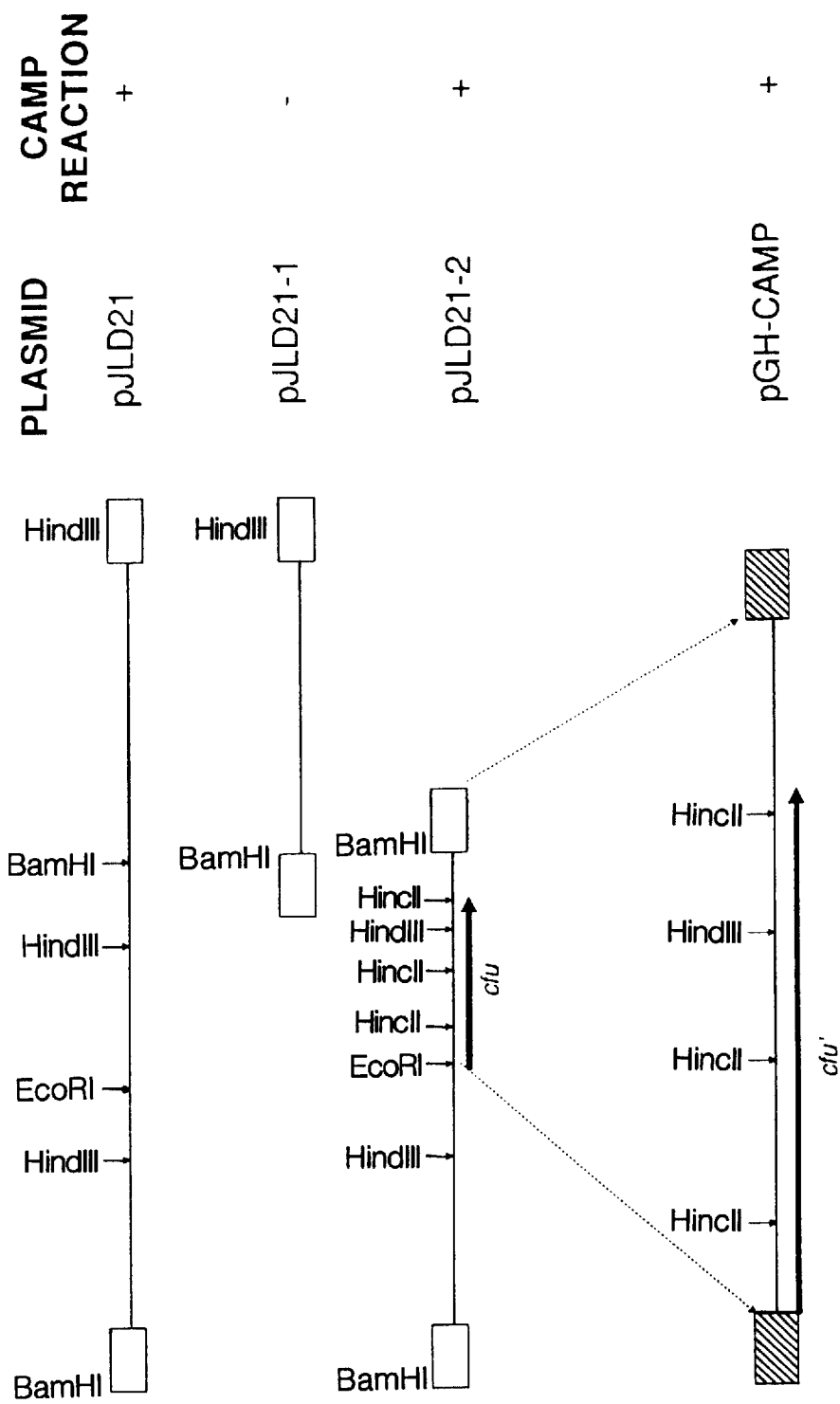

Another expression plasmid for the S. uberis CAMP factor, pGH-CAMP, was constructed as shown in FIG. 8. In particular, A 1.7 kb EcoRI-BamHI fragment of pJLD21-2 was filled in with Klenow polymerase and inserted into pGH433 which was cut by BamHI and filled in a similar fashion. Plasmid pGH433 is an expression vector containing a tac promoter, a translational start site with restriction enzyme sites allowing ligation in all three reading frames followed by stop codons in all reading frames. See, Theisen, M. and Potter, A. A. (1992) J. Bacteriol. 174:17–23.

The expression plasmids were used to transform E. coli JF1754 (described above). The CAMP factor was prepared from inclusion bodies as described in, e.g., Rossi-Campos et al. (1992) Vaccine 10:512–518, for use in the vaccine trials below. Briefly, bacteria were grown to mid-log phase and isopropyl-β,D-thiogalactoside (IPTG) was added and the cultures were incubated with vigorous agitation at 37° C. The bacteria were harvested by centrifugation, resuspended and frozen at −70° C. The frozen cells were thawed at room temperature and lysozyme was added. A detergent mix was then added. The viscosity was reduced by sonication and protein aggregates were harvested by centrifugation. The pellets were dissolved in a minimal volume of 4M guanidine hydrochloride. The proteins were analyzed by sodium dodecyl sulfate-polyacrylamide gel electrophoresis and the protein concentration was estimated by comparing the intensity of the coomassie blue-stained bands to a bovine serum albumin standard.

EXAMPLE 2

Nucleotide Sequence of S. uberis CAMP Factor Gene

To obtain the nucleotide sequence of the S. uberis CAMP factor gene, each of the EcoRI, HindIII, HincII and SacI fragments of pJLD21-2 was individually cloned into pTZ18R. Fragments were sequenced in both orientations as shown in FIG. 1. The complete DNA sequence is presented in FIGS. 4A–4C (SEQ ID NO: 1–2). An open reading frame beginning with an ATG codon located at positions 157 to 159 and terminating with the TAA stop codon at positions 925 to 927 was found which could encode a 256-residue polypeptide with a calculated molecular weight of 28,363. The ATG start codon is preceded by the purine-rich sequence AAGAGG, which serves as a ribosome binding site in E. coli (Stormo et al. (1982) Nucleic Acids Res. 10:2971–2996).

EXAMPLE 3

Primer Extension Analysis

Figure 5:
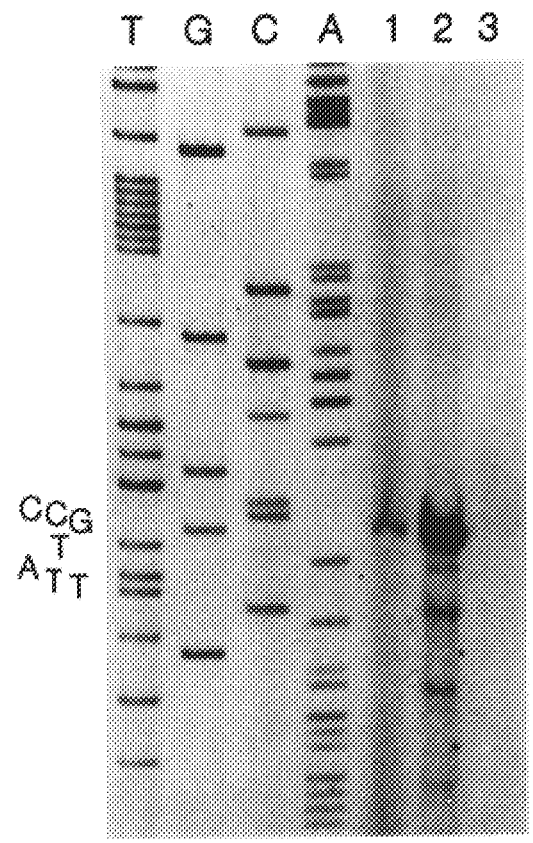

To localize the start site of transcription and the promoter region of the CAMP factor gene, primer extension analysis of RNA from S. uberis (ATCC 9927), E. coli JF1754 (pJLD21) and E. coli JF1754(pTZ18R) was done by using a synthetic oligonucleotide complementary to the DNA sequence from position 201 to 184. A strong primer extension product corresponding to base 91 ("T") was identified from both S. uberis and E. coli JF1754(pJLD21), but not from E. coli JF1754(pTZ18R) (FIG. 5). This data indicates that there is a major transcript of S. uberis CAMP factor gene initiated with an "A" residue (+1 in FIGS. 4A–4C; SEQ ID NO: 1–2). Both −10 and −35 regions, characteristic of E. coli promoters[29], were identified at the upstream of the transcriptional start site (FIGS. 4A–4C; SEQ ID NO: 3–4).

EXAMPLE 4

Comparison of the S. uberis CAMP Factor with S. agalactiae CAMP Factor

To compare the S. uberis CAMP factor with protein B of S. agalactiae, a concentrated culture supernatant of S. agalactiae containing protein B (Jürgens et al. (1985) J. Chrom. 348:363–370) was separated by SDS-PAGE and analyzed by immunoblotting with antibodies against the purified S. uberis CAMP factor. A 25 kDa protein band from the S. agalactiae supernatant (FIG. 3A, lane 4) reacted in the immunoblot (FIG. 3B, lane 4). This data indicated that monospecific antibodies raised against the S. uberis CAMP factor could cross-react with S. agalactiae protein B. This is not surprising since alignment of the 226-amino acid sequence of the S. agalactiae CAMP factor with the deduced 256 amino acids of the S. uberis CAMP factor showed 66.4% identical residues (FIG. 6; SEQ ID NOS: 3–4).

EXAMPLE 5

Distribution of CAMP Factor Genes in Eight S. uberis Strains

Figure 7:
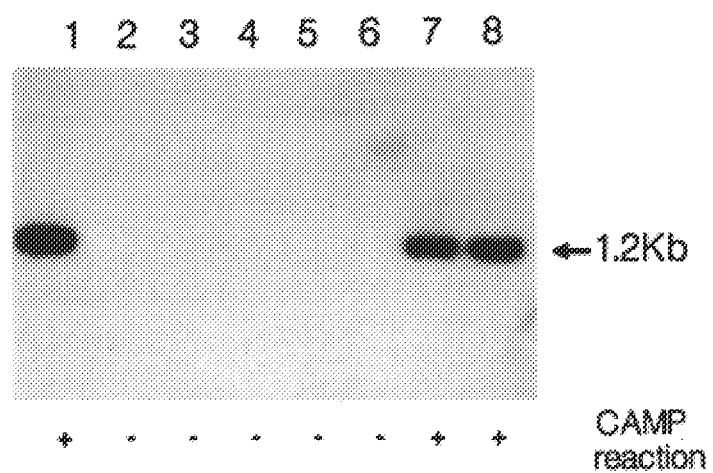

To study the distribution of the CAMP factor gene in other S. uberis strains, chromosomal DNA prepared from eight S. uberis strains was digested with the restriction endonuclease HindIII and separated on an agarose gel. Southern blot analysis with the 576 bp HindIII-EcoRI fragment of pJLD21 as a probe (FIG. 1) showed that a fragment identical in size to the HindIII fragment (1.2 kb) in pJLD21 was present in three S. uberis strains which were CAMP-reaction positive, while none of the CAMP reaction negative strains reacted with the probe (FIG. 7). Thus, the CAMP-negative strains do not contain the cfu gene.

EXAMPLE 6

Immunogenicity and Protective Capability of the CAMP Factor

S. uberis CAMP factor, encoded by pGH-CAMP, was prepared from inclusion bodies as described in Example 1. The antigen was formulated in VSA3 adjuvant which is a combination of Emulsigen Plus™ from MVP Laboratories, Ralston, Nebr. and Dimethyldioctadecyl ammonium bromide (DDA) from Kodak (Rochester, N.Y.). The final concentration was 25 µg per ml of CAMP factor, 30% Emulsigen Plus, 0.9% Tween-80, and 2.5 mg per ml of DDA. The dose volume was 2 cc containing 50 µg of recombinant antigen.

Fifteen healthy lactating dairy cows from the Pennsylvania State University Mastitis Research Herd were used to study the ability of the S. uberis CAMP factor to protect cows from mastitis. Animals were assigned to two groups of five cows. Treatment groups consisted of 1) experimental, given the vaccine including the S. uberis CAMP factor, administered intramuscularly at dry off and again 28 days later, and 2) placebo (vehicle) administered via intramuscular injection at dry off and again 28 days later.

All animals were challenged in one quarter with S. uberis on day four of lactation. Milk and blood samples were obtained as outlined in Table 1.

TABLE 1

Sampling Schedule

| TIME | SAMPLE |
| --- | --- |
| dry off, D − 0 | serum, milk, immunization |
| 14 days dry, D + 14 | serum |
| 28 days dry, D + 28 | serum, immunization |
| 52 days dry, D + 52 | serum |
| calving, C − 0 | serum, milk, bacteriology |
| 4 days lactation, CH − 0 | serum, milk, bacteriology, challenge |
| 5 days lactation, CH + 1 | bacteriology |
| 6 days lactation, CH + 2 | bacteriology |
| 7 days lactation, CH + 3 | serum, milk, bacteriology |
| 14 days lactation, CH + 10 | serum, milk, bacteriology |
| 21 days lactation, CH + 17 | serum, milk, bacteriology |

The challenge strain of S. uberis (ATCC strain 9927) was obtained from a clinical case of bovine mastitis. The stock culture of S. uberis was grown in tryptic soy broth and individual aliquot were stored at −70° C. on blood beads until needed. The bacterial challenge was prepared by rolling the stock bead cultures onto esculin blood agar plates containing 5% whole blood. After 24 hours incubation at 37° C., a single colony was used to inoculate 100 ml of Ultra High Temperature pasteurized (UHT) milk and incubated for 12 hours at 37° C. The 24 hour culture was mixed well and a 100 µl aliquot was removed to inoculate a second 100 ml of UHT milk. After a second 9 hour incubation at 37° C., the culture was serially diluted in 10-fold increments using sterile saline. The colony forming units (CFU) per ml of each dilution was determined by absorbance on a spectrophotometer and confirmed by plate pouring onto blood agar plates. The dilution containing 200 CFR of S. uberis per ml of saline was selected for each challenge.

Total Ig titers for CAMP factor were determined by an indirect ELISA. Immunlon-2 plates were coated with antigen in carbonate buffer. Prior to use, the plates were blocked with TBST (100 mM Tris Cl, pH 8.0; 150 mM NaCl; 0.05% Tween-20) and 3% BSA for 1 hour. After blocking, the plates were washed with distilled water. Serum and milk samples were serially diluted in 3-fold increments using TBST containing 1% BSA. Rabbit antisera for S. uberis CAMP factor was also diluted and served as a positive control. Negative control samples contained TBST with 1% BSA. The diluted samples and controls were transferred to the coated plates and were incubated for 1 hour at room temperature. The plates were washed thoroughly with distilled water and all wells were incubated with a horse radish peroxidase conjugate of goat anti-IgG diluted 1:2000 in TBST containing 1% BSA. Following a 1 hour incubation at room temperature, the plates were washed with distilled water. The amount of antibody present in samples was visualized using ABT substrate. The titers of each sample were based on the absorbance reading at 405 nm with a reference wavelength of 495 nm. A positive reading for samples was one in which the absorbance was two times the absorbance of the blank (negative control). Titers were determined by taking the reciprocal of the last dilution giving a positive reading. Consistency among assay plates was monitored by the absorbance reading of positive controls.

The results are shown in TABLES 2 and 3. As can be seen, antibody titers were greater in the vaccinated animals than in the placebo group.

TABLE 2

Average Serum Titers Following Experimental Challenge with S. uberis

| Treatment Group | Before Immunization | Before Challenge | After Challenge |
|---|---|---|---|
| Placebo A[1] | 6.75 | 45.0 | 45.0 |
| CAMP factor | 3.00 | 819.00 | 445.50 |

[1]Serum titers of samples obtained from placebo immunized animals screened for CAMP factor.

TABLE 3

Average Lacteal Antibody Titers Following Experimental Challenge with S. uberis

| Treatment Group | Before Immunization | Before Challenge | After Challenge |
|---|---|---|---|
| Placebo A[1] | 0.00 | 0.00 | 1.33 |
| CAMP factor | 8.00 | 288.00 | 42.50 |

[1]Lacteal antibody titers of samples obtained from placebo immunized animals screened for CAMP factor.

Somatic cell counts are a traditional measure of mastitis in cows. Accordingly, milk was assayed for somatic cells using standard assay. Results are shown in TABLE 4. As is readily apparent, immunized animals had a somatic cell count within normal limits while the placebo group had cell counts indicating the presence of mastitis. Thus, the CAMP factor vaccine was effective in preventing mastitis.

TABLE 4

Average Milk Somatic Cell Counts Following Experimental Challenge with S. uberis

| Treatment Group | Before Challenge[1] | After Challenge[2] |
|---|---|---|
| | 1000 cells/ml milk | |
| Placebo A | 130.50 | 2825.25 |
| CAMP factor | 251.75 | 51.50 |

[1]Milk SCC obtained from quarters immediately prior to intramammary challenge with S. uberis
[2]Milk SCC obtained from quarters 3 days following intramammary challenge with S. uberis Thus, immunogenic CAMP factors are disclosed, as are methods of making and using the same. Although preferred embodiments of the subject invention have been described in some detail, it is understood that obvious variations can be made without departing from the spirit and the scope of the invention as defined by the appended claims.

---

We claim:

1. A method of treating or preventing a streptococcal infection in a ruminant, bovine or equine subject comprising administering to said subject a therapeutically effective amount of a vaccine composition comprising a pharmaceutically acceptable vehicle and at least one isolated, immunogenic *Streptococcus uberis* cohemolysin (CAMP factor) polypeptide capable of reducing somatic cell counts in milk, wherein said CAMP factor polypeptide comprises an amino acid sequence selected from the group consisting of: (a) the amino acid sequence shown at positions 1 through 256, inclusive, of SEQ ID NO:2; or an immunogenic fragment thereof comprising at least about 10 contiguous amino acids therefrom; (b) the amino acid sequence shown at positions 29 through 256, inclusive, of SEQ ID NO:2; and an immunogenic fragment thereof comprising at least about 10 contiguous amino acids therefrom.

2. A method of treating or preventing mastitis in a ruminant, bovine or equine subject comprising administering to said subject a therapeutically effective amount of a vaccine composition comprising a pharmaceutically acceptable vehicle and at least one isolated, immunogenic *Streptococcus uberis* cohemolysin (CAMP factor) polypeptide capable of reducing somatic cell counts in milk, wherein said CAMP factor polypeptide comprises an amino acid sequence selected from the group consisting of: (a) the amino acid sequence shown at positions 1 through 256, inclusive, of SEQ ID NO:2; an immunogenic fragment thereof comprising at least about 10 contiguous amino acids therefrom; (b) the amino acid sequence shown at positions 29 through 256, inclusive, of SEQ ID NO: 2; and an immunogenic fragment thereof comprising at least about 10 contiguous amino acids therefrom.

3. The method of claim 1 wherein said vaccine composition further comprises an adjuvant.

4. The method of claim 2 wherein said vaccine composition further comprises an adjuvant.

5. The method of claim 4 wherein said CAMP factor polypeptide comprises the amino acid sequence shown at positions 1 through 25, inclusive, of SEQ ID NO;2.

6. The method of claim 4 wherein said CAMP factor polypeptide comprises the amino acid sequence shown at positions 29 through 256, inclusive, of SEQ ID NO:2.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1191 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 157..924

( x i ) SEQUENCE DESCRIPTION: SEQ ID NO:1:

```
AATGAACATA  AAATAAAAAT  TAATAATTAT  ATATTTTAT  GATAATCACA  TATATTTGAC           60

TTAAAAAAAT  TGTTACTGTA  TGATACAGGC  ATAAGTACTT  ATTTATTTTA  TAGATTGCAA          120

TTTATAAACA  ATTATATTTT  TCAAAGAGGA  ATGCTT  ATG  GAA  TTC  AAA  AAG  TTA        174
                                           Met  Glu  Phe  Lys  Lys  Leu
                                            1                     5

CTT  TAT  TTA  ACT  GGT  TCA  ATC  GCA  GGA  ATT  ACT  TTA  TTT  TCC  CCA  ATT  222
Leu  Tyr  Leu  Thr  Gly  Ser  Ile  Ala  Gly  Ile  Thr  Leu  Phe  Ser  Pro  Ile
              10                        15                      20

TTA  ACA  AGT  GTC  CAA  GCA  AAT  CAA  ATA  AAT  GTT  AGT  CAA  CCA  TCT  AAT  270
Leu  Thr  Ser  Val  Gln  Ala  Asn  Gln  Ile  Asn  Val  Ser  Gln  Pro  Ser  Asn
          25                        30                      35
```

| | | | | | | | | | | | | | | | | |
|---|---|---|---|---|---|---|---|---|---|---|---|---|---|---|---|---|
| AAT | GAA | AGT | AAT | GTT | ATT | TCA | CAG | AAA | AAA | GAA | GAA | ATT | GAT | AAT | AGT | 318 |
| Asn | Glu | Ser | Asn | Val | Ile | Ser | Gln | Lys | Lys | Glu | Glu | Ile | Asp | Asn | Ser | |
| | | 40 | | | | | 45 | | | | | 50 | | | | |
| CTA | AAT | CAG | GAA | AGT | GCT | CAA | CTA | TAT | GCC | TTG | AAA | GAA | GAT | GTT | AAA | 366 |
| Leu | Asn | Gln | Glu | Ser | Ala | Gln | Leu | Tyr | Ala | Leu | Lys | Glu | Asp | Val | Lys | |
| 55 | | | | | 60 | | | | | 65 | | | | | 70 | |
| GGA | ACT | GAG | AAA | GAA | CAA | TCA | GTT | AAT | TCA | GCA | ATT | TCA | GCT | GTT | GAA | 414 |
| Gly | Thr | Glu | Lys | Glu | Gln | Ser | Val | Asn | Ser | Ala | Ile | Ser | Ala | Val | Glu | |
| | | | | 75 | | | | | 80 | | | | | 85 | | |
| AAT | TTA | AAA | ACT | TCA | CTT | AGA | GCT | AAT | CCT | GAA | ACA | ATT | TAT | GAT | TTA | 462 |
| Asn | Leu | Lys | Thr | Ser | Leu | Arg | Ala | Asn | Pro | Glu | Thr | Ile | Tyr | Asp | Leu | |
| | | | 90 | | | | | 95 | | | | | 100 | | | |
| AAT | TCG | ATT | GGA | ACA | AGA | GTA | GAA | GCA | ATC | TCT | GAC | GTG | ATT | CAA | GCA | 510 |
| Asn | Ser | Ile | Gly | Thr | Arg | Val | Glu | Ala | Ile | Ser | Asp | Val | Ile | Gln | Ala | |
| | | 105 | | | | | 110 | | | | | 115 | | | | |
| ATT | GTT | TTT | TCA | ACG | CAA | CAG | TTA | ACA | AAT | AAA | GTT | GAT | CAA | GCT | CAC | 558 |
| Ile | Val | Phe | Ser | Thr | Gln | Gln | Leu | Thr | Asn | Lys | Val | Asp | Gln | Ala | His | |
| | 120 | | | | | 125 | | | | | 130 | | | | | |
| ATT | GAT | ATG | GGA | TTT | GCT | ATT | ACG | AAA | TTA | CTT | ATT | CGC | ATT | GCA | GAC | 606 |
| Ile | Asp | Met | Gly | Phe | Ala | Ile | Thr | Lys | Leu | Leu | Ile | Arg | Ile | Ala | Asp | |
| 135 | | | | | 140 | | | | | 145 | | | | | 150 | |
| CCA | TTT | GCT | TCA | AAT | GAA | TCC | ATT | AAA | GGG | CAA | GTC | GAA | GCT | GTT | AAA | 654 |
| Pro | Phe | Ala | Ser | Asn | Glu | Ser | Ile | Lys | Gly | Gln | Val | Glu | Ala | Val | Lys | |
| | | | | 155 | | | | | 160 | | | | | 165 | | |
| CAA | GTG | CAA | GCG | ACT | GTG | CTT | ACC | TAT | CCC | GAT | TTG | CAG | CCT | ACG | GAT | 702 |
| Gln | Val | Gln | Ala | Thr | Val | Leu | Thr | Tyr | Pro | Asp | Leu | Gln | Pro | Thr | Asp | |
| | | | 170 | | | | | 175 | | | | | 180 | | | |
| AGA | GCA | ACT | ATT | TAC | GTT | AAA | TCA | AAA | TTA | GAC | AAG | CTT | ATT | TGG | CAA | 750 |
| Arg | Ala | Thr | Ile | Tyr | Val | Lys | Ser | Lys | Leu | Asp | Lys | Leu | Ile | Trp | Gln | |
| | | 185 | | | | | 190 | | | | | 195 | | | | |
| ACA | AGA | ATT | ACC | AGA | GAT | CAA | AAA | GTT | CTT | AAT | GTA | AAG | AGT | TTT | GAA | 798 |
| Thr | Arg | Ile | Thr | Arg | Asp | Gln | Lys | Val | Leu | Asn | Val | Lys | Ser | Phe | Glu | |
| | 200 | | | | | 205 | | | | | 210 | | | | | |
| GTT | TAT | CAT | CAA | TTA | AAT | AAA | GCT | ATC | ACA | CAT | GCA | GTA | GGT | GTA | CAA | 846 |
| Val | Tyr | His | Gln | Leu | Asn | Lys | Ala | Ile | Thr | His | Ala | Val | Gly | Val | Gln | |
| 215 | | | | | 220 | | | | | 225 | | | | | 230 | |
| TTA | AAT | CCA | ACT | GTA | ACA | GTT | GCA | CAA | GTT | GAC | CAA | GAA | ATC | AAA | GTG | 894 |
| Leu | Asn | Pro | Thr | Val | Thr | Val | Ala | Gln | Val | Asp | Gln | Glu | Ile | Lys | Val | |
| | | | | 235 | | | | | 240 | | | | | 245 | | |
| CTA | CAA | GAA | GCA | TTA | AAT | ACT | GCT | CTA | CAG | TAAGGTAGAG | ATTGAATTGA | | | | | 944 |
| Leu | Gln | Glu | Ala | Leu | Asn | Thr | Ala | Leu | Gln | | | | | | | |
| | | | 250 | | | | | 255 | | | | | | | | |

| | | |
|---|---|---|
| CGTATTAAAA AGGACTGGAA TTTATTAATT TCAGTCCTTT AGAATTTTTA TTTAGCTGAT | 1004 |
| TTACTTGTTG AAGAGATTTG GTGGAAAATC AAGTACCATA CTTCATTTCT CCTCCAAATA | 1064 |
| CTTGTATGTC GATTCCCTTC TAAAACATAG CTAATTAGTT TAGTTTTCTG GCTAATAGAT | 1124 |
| TGTACATGAA ATTGTTCAAA ATTACTAGGG TAAAAGGTTT TTCTTTTTAT AAATTCATCA | 1184 |
| TGACTAT | 1191 |

( 2 ) INFORMATION FOR SEQ ID NO:2:

( i ) SEQUENCE CHARACTERISTICS:
        ( A ) LENGTH: 256 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Glu | Phe | Lys | Lys | Leu | Leu | Tyr | Leu | Thr | Gly | Ser | Ile | Ala | Gly | Ile |
| 1 | | | | 5 | | | | | 10 | | | | | 15 | |

```
Thr  Leu  Phe  Ser  Pro  Ile  Leu  Thr  Ser  Val  Gln  Ala  Asn  Gln  Ile  Asn
               20                       25                      30

Val  Ser  Gln  Pro  Ser  Asn  Asn  Glu  Ser  Asn  Val  Ile  Ser  Gln  Lys  Lys
               35                  40                           45

Glu  Glu  Ile  Asp  Asn  Ser  Leu  Asn  Gln  Glu  Ser  Ala  Gln  Leu  Tyr  Ala
     50                            55                      60

Leu  Lys  Glu  Asp  Val  Lys  Gly  Thr  Glu  Lys  Gln  Ser  Val  Asn  Ser
65                       70                      75                           80

Ala  Ile  Ser  Ala  Val  Glu  Asn  Leu  Lys  Thr  Ser  Leu  Arg  Ala  Asn  Pro
                    85                       90                           95

Glu  Thr  Ile  Tyr  Asp  Leu  Asn  Ser  Ile  Gly  Thr  Arg  Val  Glu  Ala  Ile
               100                      105                     110

Ser  Asp  Val  Ile  Gln  Ala  Ile  Val  Phe  Ser  Thr  Gln  Gln  Leu  Thr  Asn
          115                      120                     125

Lys  Val  Asp  Gln  Ala  His  Ile  Asp  Met  Gly  Phe  Ala  Ile  Thr  Lys  Leu
     130                      135                          140

Leu  Ile  Arg  Ile  Ala  Asp  Pro  Phe  Ala  Ser  Asn  Glu  Ser  Ile  Lys  Gly
145                           150                 155                         160

Gln  Val  Glu  Ala  Val  Lys  Gln  Val  Gln  Ala  Thr  Val  Leu  Thr  Tyr  Pro
                    165                      170                     175

Asp  Leu  Gln  Pro  Thr  Asp  Arg  Ala  Thr  Ile  Tyr  Val  Lys  Ser  Lys  Leu
               180                      185                     190

Asp  Lys  Leu  Ile  Trp  Gln  Thr  Arg  Ile  Thr  Arg  Asp  Gln  Lys  Val  Leu
          195                      200                     205

Asn  Val  Lys  Ser  Phe  Glu  Val  Tyr  His  Gln  Leu  Asn  Lys  Ala  Ile  Thr
     210                           215                     220

His  Ala  Val  Gly  Val  Gln  Leu  Asn  Pro  Thr  Val  Thr  Val  Ala  Gln  Val
225                           230                      235                    240

Asp  Gln  Glu  Ile  Lys  Val  Leu  Gln  Glu  Ala  Leu  Asn  Thr  Ala  Leu  Gln
                    245                      250                     255
```

( 2 ) INFORMATION FOR SEQ ID NO:3:

( i ) SEQUENCE CHARACTERISTICS:
        ( A ) LENGTH: 256 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met  Glu  Phe  Lys  Lys  Leu  Leu  Tyr  Leu  Thr  Gly  Ser  Ile  Ala  Gly  Ile
1                   5                       10                          15

Thr  Leu  Phe  Ser  Pro  Ile  Leu  Thr  Ser  Val  Gln  Ala  Asn  Gln  Ile  Asn
               20                       25                      30

Val  Ser  Gln  Pro  Ser  Asn  Asn  Glu  Ser  Asn  Val  Ile  Ser  Gln  Lys  Lys
               35                  40                           45

Glu  Glu  Ile  Asp  Asn  Ser  Leu  Asn  Gln  Glu  Ser  Ala  Gln  Leu  Tyr  Ala
     50                            55                      60

Leu  Lys  Glu  Asp  Val  Lys  Gly  Thr  Glu  Lys  Gln  Ser  Val  Asn  Ser
65                       70                      75                           80

Ala  Ile  Ser  Ala  Val  Glu  Asn  Leu  Lys  Thr  Ser  Leu  Arg  Ala  Asn  Pro
                    85                       90                           95

Glu  Thr  Ile  Tyr  Asp  Leu  Asn  Ser  Ile  Gly  Thr  Arg  Val  Glu  Ala  Ile
               100                      105                     110
```

```
Ser  Asp  Val  Ile  Gln  Ala  Ile  Val  Phe  Ser  Thr  Gln  Gln  Leu  Thr  Asn
          115                 120                      125

Lys  Val  Asp  Gln  Ala  His  Ile  Asp  Met  Gly  Phe  Ala  Ile  Thr  Lys  Leu
     130                 135                      140

Leu  Ile  Arg  Ile  Ala  Asp  Pro  Phe  Ala  Ser  Asn  Glu  Ser  Ile  Lys  Gly
145                      150                      155                      160

Gln  Val  Glu  Ala  Val  Lys  Gln  Val  Gln  Ala  Thr  Val  Leu  Thr  Tyr  Pro
                    165                      170                      175

Asp  Leu  Gln  Pro  Thr  Asp  Arg  Ala  Thr  Ile  Tyr  Val  Lys  Ser  Lys  Leu
               180                      185                      190

Asp  Lys  Leu  Ile  Trp  Gln  Thr  Arg  Ile  Thr  Arg  Asp  Gln  Lys  Val  Leu
          195                      200                      205

Asn  Val  Lys  Ser  Phe  Glu  Val  Tyr  His  Gln  Leu  Asn  Lys  Ala  Ile  Thr
     210                      215                      220

His  Ala  Val  Gly  Val  Gln  Leu  Asn  Pro  Thr  Val  Thr  Val  Ala  Gln  Val
225                      230                      235                      240

Asp  Gln  Glu  Ile  Lys  Val  Leu  Gln  Glu  Ala  Leu  Asn  Thr  Ala  Leu  Gln
               245                      250                      255
```

( 2 ) INFORMATION FOR SEQ ID NO:4:

( i ) SEQUENCE CHARACTERISTICS:
        ( A ) LENGTH: 226 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Asp  Gln  Val  Thr  Thr  Pro  Gln  Val  Val  Asn  His  Val  Asn  Ser  Asn  Asn
1                   5                    10                       15

Gln  Ala  Gln  Gln  Met  Ala  Gln  Lys  Leu  Asp  Gln  Asp  Ser  Ile  Gln  Leu
               20                       25                       30

Arg  Asn  Ile  Lys  Asp  Asn  Val  Gln  Gly  Thr  Asp  Tyr  Glu  Lys  Pro  Val
          35                       40                       45

Asn  Glu  Ala  Ile  Thr  Ser  Val  Glu  Lys  Leu  Lys  Thr  Ser  Leu  Arg  Ala
     50                       55                       60

Asn  Ser  Glu  Thr  Val  Tyr  Asp  Leu  Asn  Ser  Ile  Gly  Ser  Arg  Val  Glu
65                       70                       75                       80

Ala  Leu  Thr  Asp  Val  Ile  Glu  Ala  Ile  Thr  Phe  Ser  Thr  Gln  His  Leu
                    85                       90                       95

Ala  Asn  Lys  Val  Ser  Gln  Ala  Asn  Ile  Asp  Met  Gly  Phe  Gly  Ile  Thr
               100                      105                      110

Lys  Leu  Val  Ile  Arg  Ile  Leu  Asp  Pro  Phe  Ala  Ser  Val  Asp  Ser  Ile
          115                      120                      125

Lys  Ala  Gln  Val  Asn  Asp  Val  Lys  Ala  Leu  Glu  Gln  Lys  Val  Leu  Thr
     130                      135                      140

Tyr  Pro  Asp  Leu  Lys  Pro  Thr  Asp  Arg  Ala  Thr  Ile  Tyr  Thr  Lys  Ser
145                      150                      155                      160

Lys  Leu  Asp  Lys  Glu  Ile  Trp  Asn  Thr  Arg  Phe  Thr  Arg  Asp  Lys  Lys
                    165                      170                      175

Val  Leu  Asn  Val  Lys  Glu  Phe  Lys  Val  Tyr  Asn  Thr  Leu  Asn  Lys  Ala
               180                      185                      190

Ile  Thr  His  Ala  Val  Gly  Val  Gln  Leu  Asn  Pro  Asn  Val  Thr  Val  Gln
          195                      200                      205

Gln  Val  Asp  Gln  Glu  Ile  Val  Thr  Leu  Gln  Ala  Ala  Leu  Gln  Thr  Ala
```

| 210 | 215 | 220 |

Leu Lys
225